United States Patent
Lieblich et al.

(10) Patent No.: US 11,064,979 B2
(45) Date of Patent: Jul. 20, 2021

(54) REAL-TIME ANATOMICALLY BASED DEFORMATION MAPPING AND CORRECTION

(71) Applicant: Analogic Corporation, Peabody, MA (US)

(72) Inventors: David Lieblich, Worcester, MA (US); Zhaolin Li, Malden, MA (US)

(73) Assignee: Analogic Corporation, Peabody, MA (US)

( * ) Notice: Subject to any disclaimer, the term of this patent is extended or adjusted under 35 U.S.C. 154(b) by 865 days.

(21) Appl. No.: 15/155,397

(22) Filed: May 16, 2016

(65) Prior Publication Data
US 2017/0325785 A1   Nov. 16, 2017

(51) Int. Cl.
*A61B 8/00*   (2006.01)
*A61B 8/08*   (2006.01)
(Continued)

(52) U.S. Cl.
CPC .............. *A61B 8/54* (2013.01); *A61B 8/14* (2013.01); *A61B 8/4483* (2013.01); *A61B 8/461* (2013.01);
(Continued)

(58) Field of Classification Search
CPC ....... G06T 19/00; G06T 7/33; G06T 2210/41; G06T 2207/30004; G06T 2207/10132;
(Continued)

(56) References Cited

U.S. PATENT DOCUMENTS 5,428,448 A * 6/1995 Albert-Garcia .... G01B 11/2433
33/200
5,474,070 A * 12/1995 Ophir ................... A61B 5/0048
600/437
(Continued)

FOREIGN PATENT DOCUMENTS

WO   WO-2008122056 A2 * 10/2008 ........... A61N 5/0601

OTHER PUBLICATIONS

Goerres, G. W., Kamel, E., Heidelberg, T. H., Schwitter, M. R., Burger, C., & von Schulthess, G.,K. (2002). PET-CT image co registration in the thorax: Influence of respiration. European Journal of Nuclear Medicine and Molecular Imaging, 29(3), 351-60.doi:http://dx.doi.org/10.1007/s00259-001-0710-4.*
(Continued)

*Primary Examiner* — Serkan Akar
*Assistant Examiner* — Aminah Asghar
(74) *Attorney, Agent, or Firm* — Anthony M. Del Zoppo, III; Daugherty & Del Zoppo, Co. LPA (57)   ABSTRACT

A method includes generating a real-time ultrasound image of anatomy of interest. At least a sub-portion of the anatomy of interest is deformed from an initial location to a different location by pressure applied by an external force. The method further includes obtaining a 2-D slice, which corresponds to a same plane as the real-time ultrasound image, from 3-D reference image data, wherein a corresponding sub-portion is at the initial location. The method further includes determining displacement fields for the sub-portion from the sub-portion, the corresponding sub-portion and other anatomy not-deformed in the real-time ultrasound image and the 3-D reference image data. The method further includes deforming the 3-D reference image data using the displacement fields, which creates deformed 3-D reference image data based on the different location.

9 Claims, 4 Drawing Sheets

(51) Int. Cl.
    *A61B 8/14*    (2006.01)
    *G06T 7/33*    (2017.01)
    *G06T 19/00*   (2011.01)
(52) U.S. Cl.
    CPC .............. *A61B 8/467* (2013.01); *A61B 8/483* (2013.01); *A61B 8/5246* (2013.01); *G06T 7/33* (2017.01); *G06T 19/00* (2013.01); *G06T 2207/10072* (2013.01); *G06T 2207/10132* (2013.01); *G06T 2207/30004* (2013.01); *G06T 2210/41* (2013.01)
(58) Field of Classification Search
    CPC ... G06T 2207/10072; G06T 7/00; A61B 8/54; A61B 8/5246; A61B 8/483; A61B 8/467; A61B 8/4483; A61B 8/14; A61B 8/461; A61B 8/0841; A61B 8/08; A61B 8/00
    See application file for complete search history.

(56) References Cited

U.S. PATENT DOCUMENTS

| | | | | |
|---|---|---|---|---|
| 2006/0052706 | A1* | 3/2006 | Hynynen | A61N 7/022 600/459 |
| 2008/0039713 | A1* | 2/2008 | Thomson | G16H 50/30 600/411 |
| 2008/0091678 | A1* | 4/2008 | Walker | G06T 7/30 |
| 2008/0186378 | A1* | 8/2008 | Shen | A61B 8/0833 348/65 |
| 2012/0155734 | A1* | 6/2012 | Barratt | G06T 7/35 382/131 |
| 2013/0324841 | A1* | 12/2013 | Kamen | A61B 8/0841 600/424 |
| 2014/0037168 | A1* | 2/2014 | Ishikawa | G06T 7/33 382/130 |
| 2015/0201910 | A1* | 7/2015 | Zhao | G06T 7/33 600/424 |
| 2016/0217560 | A1* | 7/2016 | Tahmasebi Maraghoosh | G06T 7/337 |
| 2016/0274067 | A1* | 9/2016 | Walker | G01N 29/4418 |
| 2017/0169577 | A1* | 6/2017 | Accomando | G06T 7/33 |
| 2017/0365058 | A1* | 12/2017 | Kabus | G06T 11/00 |

OTHER PUBLICATIONS

Yan, HB; HU, SM; Martin, RR. 3D Morphing Using Strain Field Interpolation. Journal of Computer Science and Technology. China, 1, 147, 2007. ISSN: 1000-9000.*

International Journal of Scientific & Engineering Research, vol. 5, Issue 6, Jun. 2014 ISSN 2229-5518; FPGA-Based 16-Channgel Digital Ultrasound Receive Beamformer, Hassan, Mawia Ahmed; p. 484, abstract.*

Mathworks® (Sign function (Signum function) (2015)).*

* cited by examiner

REAL-TIME ANATOMICALLY BASED DEFORMATION MAPPING AND CORRECTION

TECHNICAL FIELD

The following generally relates to image registration and more particularly to segmented anatomical structure based image registration, and is described with particular application to ultrasound imaging, but is also amenable to other imaging modalities.

BACKGROUND

An ultrasound imaging system has included a probe with transducer array that transmits an ultrasound beam into an examination field of view. As the beam traverses structure (e.g., in an object or subject) in the field of view, sub-portions of the beam are attenuated, scattered, and/or reflected off the structure, with some of the reflections (echoes) traversing back towards the transducer array. The transducer array receives and processes the echoes, and generates one or more images of the structure.

The resulting ultrasound images have been used to guide procedures in real-time, i.e., using presently generated images from presently acquired echoes. This has included registering a real-time image to a corresponding plane in previously (e.g., pre-procedure) generated 3-D reference anatomical image data and displaying the 3-D reference anatomical image data with the real-time ultrasound image superimposed over the corresponding plane. The displayed image data indicates a location and orientation of the transducer array with respect to the anatomy in the 3-D reference anatomical image.

However, when acquiring the real-time ultrasound image, pressure applied to the ultrasound probe, e.g., to maintain a coupling between the transducer array and the object or subject being scanned, may deform anatomical structures in the scanned region of interest. Unfortunately, when this occurs, the deformed anatomical structure may distort the registration of the real-time ultrasound image and the generated 3-D reference anatomical image data. For instance, the generated 3-D reference anatomical image data may no longer represent the current location of the anatomy if the anatomy is now deformed and therefore cannot be relied on to navigate the probe to the anatomy of interest in the 3-D volume.

SUMMARY

Aspects of the application address the above matters, and others.

In one aspect, a method includes generating a real-time ultrasound image of anatomy of interest. At least a sub-portion of the anatomy of interest is deformed from an initial location to a different location by pressure applied by an external force. The method further includes obtaining a 2-D slice, which corresponds to a same plane as the real-time ultrasound image, from 3-D reference image data, wherein a corresponding sub-portion is at the initial location. The method further includes determining displacement fields for the sub-portion from the sub-portion, the corresponding sub-portion and other anatomy not-deformed in the real-time ultrasound image and the 3-D reference image data. The method further includes deforming the 3-D reference image data using the displacement fields, which creates deformed 3-D reference image data based on the different location.

In another aspect, an apparatus includes a beamformer that generates a real-time 2-D ultrasound image from echoes received by transducer element of a transducer array. The apparatus further includes a 3-D reference image data memory that stores segmented 3-D reference image data of a volume of interest, wherein the 3-D reference image data includes a first structure at a first location and a second structure at a second location. The apparatus further includes a 3-D reference image data updater configured to warp the segmented 3-D reference image data based on the real-time 2-D ultrasound image, wherein the real-time 2-D ultrasound image includes the first structure at a third different location and the second structure is at least partially at a corresponding same second location, and wherein the first structure is displaced from the first location to the third location by pressure applied by an external force from the transducer array.

In another aspect, a non-transitory computer readable medium is encoded with computer executable instructions, which, when executed by a computer processor, causes the processor to: obtain 3-D reference image data including a first structure at a first location, determine a change in a location of the first structure in a real-time image to a second location which is different from the first location relative to the 3-D reference image data based on contours of the first structure and of second structure in the 3-D reference image data and the real-time image, wherein the second structure is at a same location in both the 3-D reference image data and the real-time image, and modify the 3-D reference image data based on the change so that the first structure is at a same location in the 3-D reference image data and in the real-time image, wherein the same location corresponds to a location of the first structure in the real-time image.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

The following generally describes an approach for registering a real-time anatomical ultrasound image and previously generated 3-D reference anatomical image data that includes a plane corresponding to the plane of the real-time anatomical image, e.g., for an image guided procedure, taking into account deformation of anatomical structures in the real-time anatomical ultrasound image, e.g., due to pressure exerted by the transducer array that acquired the echoes that were processed to generate the real-time anatomical ultrasound image. As utilized herein, a real-time 2-D ultrasound image refers to a currently or presently generated image, generated from echoes currently or presently acquired.

Figure 1:
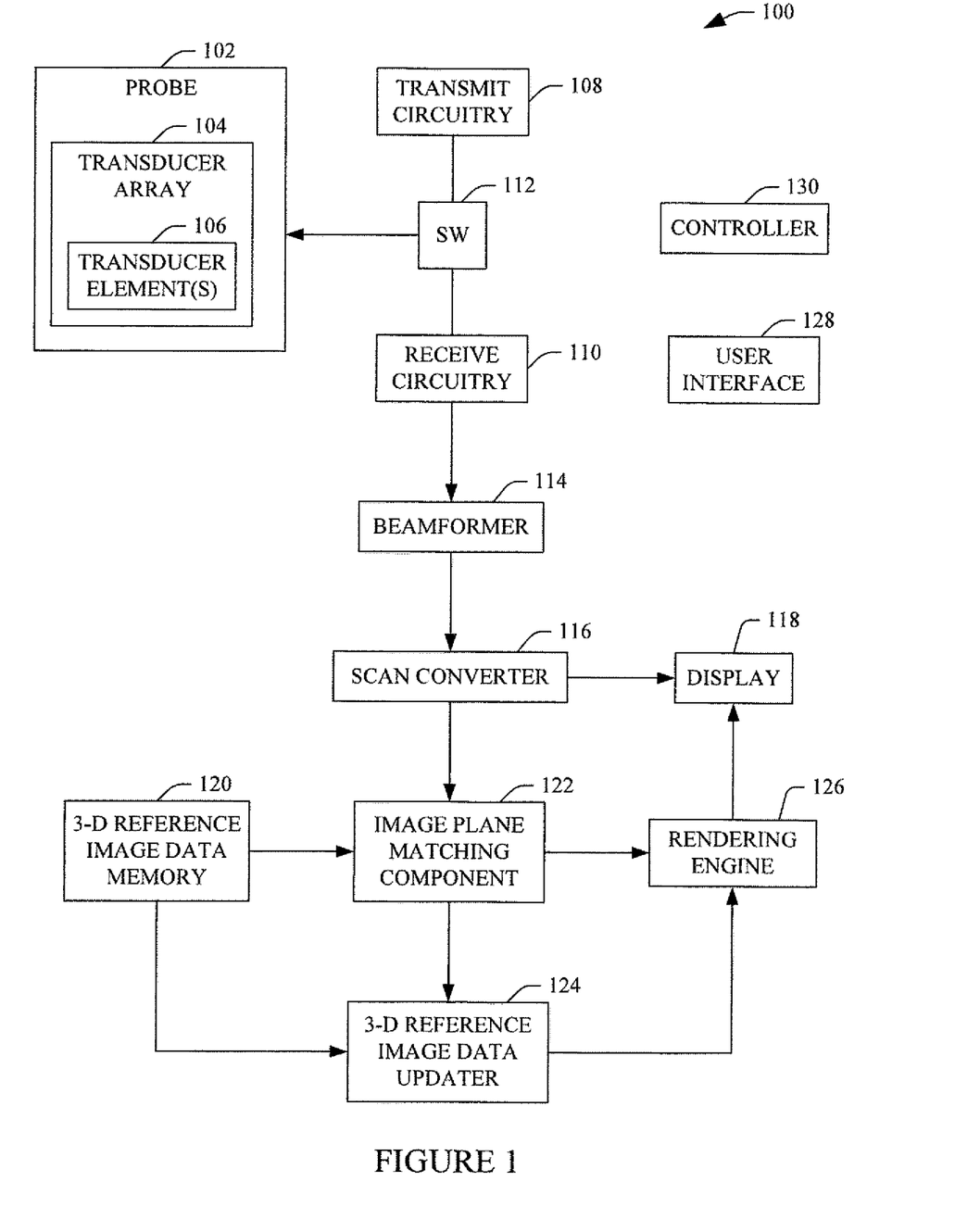
FIG. 1 schematically shows an example ultrasound imaging system with a 3-D reference image data updater.

Initially referring to FIG. 1, an ultrasound imaging system 100 includes a probe 102 housing a transducer array 104 having at least one transducer element 106. The at least one transducer element 106 is configured to convert electrical signals to an ultrasound pressured field and vice versa respectively to transmit ultrasound signals into a field of view and receive echo signals, generated in response to interaction with structure in the field of view, from the field of view. The transducer array 104 can be linear, curved (e.g., concave, convex, etc.), circular, etc., fully populated or sparse, etc.

Transmit circuitry 108 generates a set of pulses (or a pulsed signal) that are conveyed, via hardwire (e.g., through a cable) and/or wirelessly, to the transducer array 104. The set of pulses excites a set (i.e., a sub-set or all) of the at least one transducer element 106 to transmit ultrasound signals. Receive circuitry 110 receives a set of echoes (or echo signals) generated in response to a transmitted ultrasound signal interacting with structure in the field of view. A switch (SW) 112 controls whether the transmit circuitry 108 or the receive circuitry 110 is in electrical communication with the at least one transducer element 106 to transmit ultrasound signals or receive echoes.

A beamformer 114 processes the received echoes by applying time delays to echoes, weighting echoes, summing delayed and weighted echoes, and/or otherwise beamforming received echoes, creating beamformed data. In B-mode imaging, the beamformer 114 produces a sequence of focused, coherent echo samples along focused scanlines of a scanplane. The beamformer 114 may also process the scanlines to lower speckle and/or improve specular reflector delineation via spatial compounding, and/or perform other processing such as FIR filtering, IIR filtering, edge enhancement, etc.

A scan converter 116 scan converts the output of the beamformer 114 to generate data for display, e.g., by converting the data to the coordinate system of a display 118. The scan converter 116 can be configured to employ analog and/or digital scan converting techniques. The display 118 can be a light emitting diode (LED), liquid crystal display (LCD), and/or another type of display. The display 118 can be part of the ultrasound imaging system 100 or a separate device that is in electrical communication therewith via a cable, wireless communication, etc.

A 3-D reference image data memory 120 includes previous generated and segmented 3-D reference image data having one or more segmented 3-D anatomical structures. In general, the 3-D reference image data includes a 3-D volume of the anatomy in which the tissue of interest, or target tissue, is located. In one instance, 3-D reference image data corresponds to a scan performed prior to the examination procedure and can be generated by a same modality as the imaging system 100 (with the same or different settings) and/or a different modality (e.g., magnetic resonance imaging (MRI), computed tomography (CT). Known and/or other segmentation algorithms can be employed to segment the 3-D anatomical structures.

An image plane matching component 122 maps a real-time 2-D ultrasound image generated by the imaging system 100 to a corresponding image plane in the 3-D reference image data. A non-limiting example of suitable mapping is described in patent application serial number PCT/US2016/32647, filed May 16, 2016, entitled "Segmented Common Anatomical Structure Based Navigation in Ultrasound Imaging," the entirety of which is incorporated herein by reference. With this approach, at least a sub-portion (e.g., a contour) of at least one segmented structure in real-time 2-D ultrasound image is matched with at least a sub-portion of at least one segmented 3-D anatomical structure of 3-D reference image data. Other approaches are also contemplated herein. A non-limiting example of generating a 3-D volume from 2-D images acquired using a freehand probe rotation or translation is described in patent application serial number PCT/US2016/32639, filed May 16, 2016, entitled "3-D US Volume From 2-D Images from Freehand Rotation and/or Translation of Ultrasound Probe," the entirety of which is incorporated herein by reference. Other approaches are contemplated herein.

A 3-D reference image data updater updates the 3-D reference image data to account for any deformations in the anatomical structure in the real-time 2-D ultrasound image relative to the previously generated and segmented 3-D reference image data due to, e.g., pressure applied to the ultrasound probe, e.g., to maintain a coupling between the transducer array and the object or subject being scanned. As described in greater detail below, in one instance this includes identifying deformation of an anatomical structure in the real-time 2-D ultrasound image relative to segmented anatomical structure in the 3-D reference image data and determining displacement fields, based on at least one of segmented anatomical structure exterior to the displacement field induced by the deformation or segmented deformable anatomical structure (e.g., bone), and then deforming and/or warping the 3-D reference image data based on the identified displacement. This approach provides a mapping that allows deformed anatomical structure(s) to be correctly located in their deformed positions in the 3-D reference image data. As such, the approach is well-suited for image guided procedures which register one or more real-time images to one or more corresponding planes in previously generated 3-D reference anatomical image data to track a location of a probe with respect to 3-D reference anatomical image data.

A rendering engine 126 combines the real-time 2-D ultrasound image with the updated 3-D reference image data at the matched image plane and visually presents the combined image data via the display 118 and/or other display. The resulting combination identifies the location and/or orientation of the ultrasound transducer array 104 relative to the current location of the scanned anatomy using the previously acquired 3-D reference image data, which allows the clinician to use the 3-D reference image data to navigate to tissue of interest in the scanned anatomy.

A user interface (UI) 128 includes an input device(s) (e.g., a physical button, a touch screen, etc.) and/or an output device(s) (e.g., a touch screen, a display, etc.), which allow for interaction between a user and the ultrasound imaging system 100. A controller 130 controls one or more of the components 104-128 of the ultrasound imaging system 100. Such control includes controlling one or more of these components to perform the functions described herein and/or other functions.

In the illustrated example, at least one of the components of the system 100 (e.g., the component 124) can be implemented via one or more computer processors (e.g., a microprocessor, a control processing unit, a controller, etc.) executing one or more computer readable instructions encoded or embodied on computer readable storage medium (which excludes transitory medium), such as physical computer memory, which causes the one or more computer processors to carry out the various acts and/or other functions and/or acts. Additionally or alternatively, the one or more computer processors can execute instructions carried by transitory medium such as a signal or carrier wave.

Figure 2:
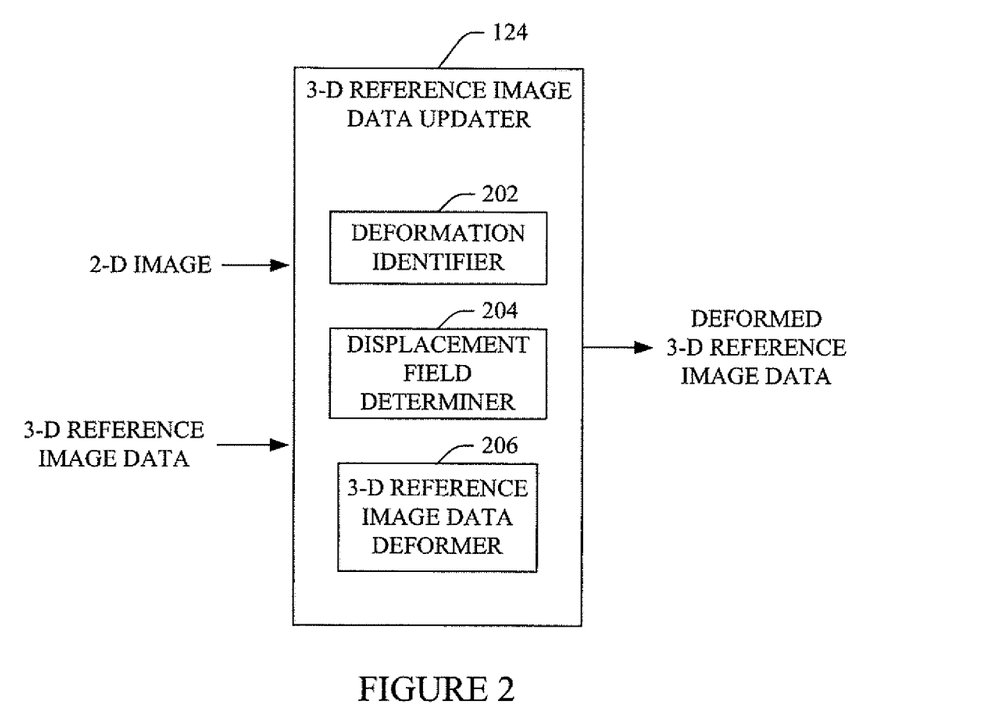
FIG. 2 schematically shows an example of the 3-D reference image data updater.

FIG. 2 schematically illustrates an example of the 3-D reference image data updater 124.

The 3-D reference image data updater 124 includes a deformation identifier 202. The deformation identifier 202 is configured to identify deformation of an anatomical structure of interest in the real-time 2-D ultrasound image relative to the 3-D reference image data. Examples of a same of set of structures in the real-time 2-D ultrasound image and the 3-D reference image data, some and/or parts of some being deformed in the real-time 2-D ultrasound image by the probe 102, are shown in FIGS. 3, 4, 5, 6, 7 and 8.

Figure 3:
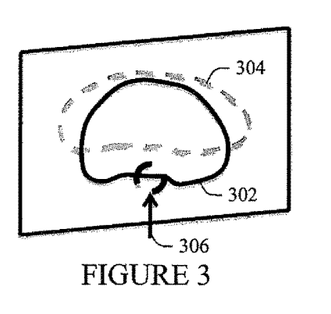
FIG. 3 shows superimposed matched axial planes, including contours for sub-portions of a same first structure, of a real-time 2-D ultrasound image and a planar slice in pre-generated 3-D reference image data that includes a plane corresponding to the plane of the real-time 2-D ultrasound image.

FIG. 3 shows superimposed matched axial planes including contours for sub-portions of a same first structure (e.g., a prostate). A first contour 302 represents the same first structure in the 3-D reference image data, and a second contour 304 represents the same first structure in the real-time 2-D ultrasound image. Arrow 306 represents a coupling force on the probe 102 which deforms at least a sub-portion of the second contour 304 of the first structure relative to the first contour 302 of the first structure.

Figure 4:
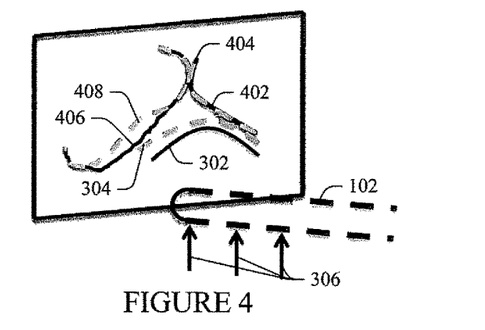
FIG. 4 shows superimposed matched sagittal planes, including contours for sub-portions of three different structures, of the real-time 2-D ultrasound image and the planar slice in the pre-generated 3-D reference image data that includes the plane corresponding to the plane of the real-time 2-D ultrasound image.

FIG. 4 shows superimposed matched sagittal planes including contours for sub-portions of three different structures, including the first structure (e.g., the prostate) of FIG. 3. A third contour 402 represents a second structure (e.g., a pubic symphysis) in the 3-D reference image data, and a fourth contour 404 represents the same second structure in the real-time 2-D ultrasound image. A fifth contour 406 represents a third structure (e.g., a bladder) in the 3-D reference image data, and a sixth contour 408 represents the same third structure in the real-time 2-D ultrasound image. The arrow 306 again represents the coupling force on the probe 102.

Returning to FIG. 2, the deformation identifier 202 can identify deformation of the first structure through one or more of FIGS. 3 and 4. In this example, the deformation of the first structure is more easily extracted from the axial plane shown in FIG. 3. In other instances, this is more easily done with the sagittal plane shown in FIG. 4. In yet other instance, this is more easily done with other planes (e.g., coronal, oblique, etc.) and/or equally in two or more different planes.

The 3-D reference image data updater 124 further includes a displacement field determiner 204. The displacement field determiner 204 is configured to determine displacement fields for structure of interest in the real-time 2-D ultrasound image and the 3-D reference image data. In this example, the displacements are extracted where undisturbed anatomy acts as reference fiducials, and the displacements reflect indentation along, at least, a finite length of the plane and not at a single point.

Figure 5:
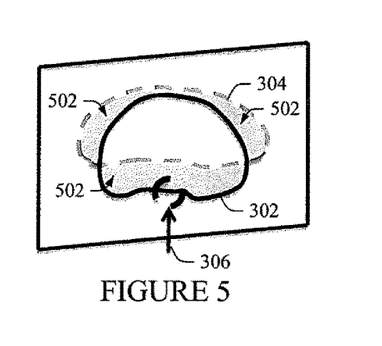
FIG. 5 shows deformation of the first structure between the real-time 2-D ultrasound image and the planar slice in the pre-generated 3-D reference image data in the matched axial planes of FIG. 3.
Figure 6:
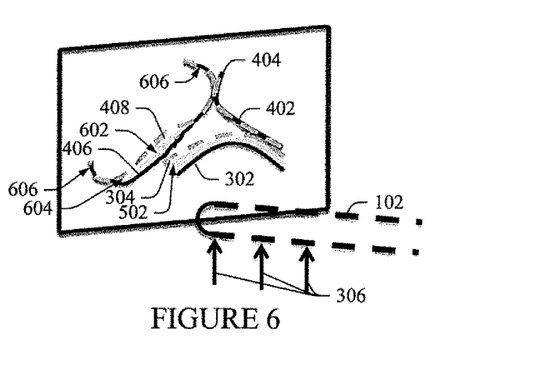
FIG. 6 shows displacement of multiple structures between the real-time 2-D ultrasound image and the planar slice in the pre-generated 3-D reference image data in the matched sagittal planes of FIG. 4.

Briefly turning to FIGS. 5 and 6, the first structure represents structure of interest that is displaced by the coupling force 306. In FIG. 5, the first structure is displaced as indicated by regions 502. FIG. 6 shows the second structure, via the overlapping contours 402 and 404, is not displaced by the coupling force 306. FIG. 6 also shows the third structure, via the contours 406 and 408, is partially displaced by the coupling force 306, as indicated by regions 602, 604 and 606, with the displacement decreasing (from region 602 to 604 to 606) to no displacement (at region 606) with distance from the applied coupling force of 306.

In one instance, distances between the first deformable structure and the second non-deformable structure are measured within the corresponding plane of the current 2D image, extracted from the 3-D reference image data. This includes determining distances between the contours 302 and 402. Distances are also measured between the first deformable structure and the second non-deformable structure in the real-time 2-D ultrasound image. This includes determining distances between the contours 304 and the corresponding 2D contour extracted from the 3D contour 404, in the 3D reference image data. The difference between these distances represents the displacement of the first deformable structure in the real-time 2-D ultrasound image relative the non-deformable structure.

In another instance, the measurement of relative material point displacements (deformation) can be done without the undeformable region but the displacements are harder to discern because the corresponding points may not be easily identified between frames, whereas the static undeformable object provides a consistent reference from frame to frame. Displacements could be measured both from just the object in, e.g., frames 1 and 2 and using the undeformed object in the same two frames to provide two measurements that could serve as a check.

Figure 7:
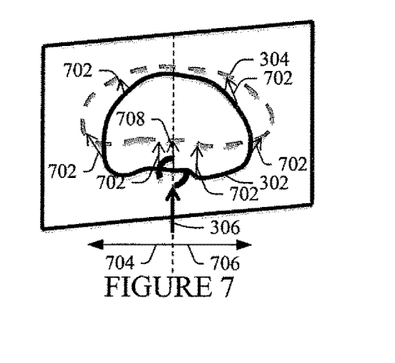
FIG. 7 shows displacement vectors for the first structure between the real-time 2-D ultrasound image and the planar slice in the pre-generated 3-D reference image data in the matched axial planes of FIGS. 3 and 5.
Figure 8:
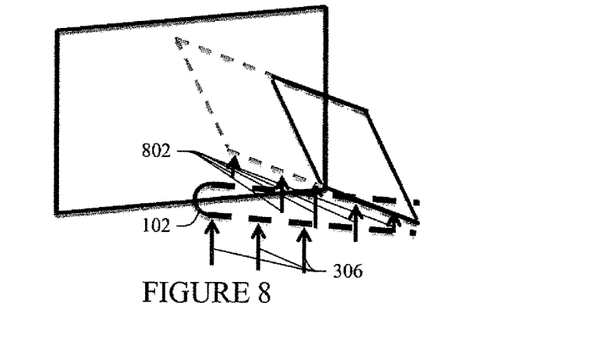
FIG. 8 shows displacement vectors in one plane for the multiple structures between the real-time 2-D ultrasound image and the planar slice in the pre-generated 3-D reference image data in the matched axial planes of FIGS. 4 and 6.

Returning to FIG. 2, in one instance the displacement field determiner 204 determines displacement fields based on the difference or differential displacements between the deformable structures and the non-deformable or partially deformable structures. FIG. 7 shows displacement vectors 702 for the deformed first structure in connection with the axial view. FIG. 8 shows displacement vectors 802 for the deformed first structure in connection with axial and sagittal views, only showing the axial plane displacement gradients.

Returning to FIG. 2, the 3-D reference image data updater 124 further includes a 3-D reference image data deformer 206. The 3-D reference image data deformer 206 is configured to deform the 3-D reference image data based on the displacement vectors so that the anatomical structure in the 3-D reference image data corresponds to the current location of that anatomical structure in the real-time 2-D ultrasound image. In one instance this is achieved by mapping the anatomical structures within the 3-D reference image data to their new, deformed locations, based on the deformation of the first structure, extracted from the axial and/or sagittal planes.

In one instance, this can be accomplished by using directional derivatives of the displacement fields, including a left direction 704 (FIG. 7) and a right direction 706 (FIG. 7), relative to a maximum displacement vector 708 (FIG. 7) in the probe plane, within the first structure, extracted from one or both planes and either assuming cylindrical symmetry of the directional derivatives or smooth transition between two differing derivatives orthogonal to a single plane. In the case of two planes with differing gradients, the gradients in two orthogonal half planes are used to derive gradients in the intervening directions as directional interpolations between them.

For example, in a simple case of a cylindrical probe with a hemispherical endcap pressing against an anatomical structure along a sagittal plane (plane intersecting the axis of the cylindrical probe), the primary component of deformation will be a compressional deformation in the direction of displacement of the probe within the sagittal plane. If we indicate this displacement component as $\vec{U}_y$ where the y-axis is one axis of the Cartesian coordinate system defining the sagittal plane (the other being the z axis, directed along the probe axis), then this displacement will decay as we move away from the probe end. If, for example we move along the positive z-axis, the decay would be represented by $$\frac{\partial \vec{U}_y}{\partial z_+},$$

where the "+" sign indicates the positive z-coordinate axis direction of a coordinate system tied to the center of the hemispherical cap and with the y-axis intersecting the sagittal image plane of the transducer head.

Similarly, the displacement decays perpendicular to the sagittal plane, in the axial plane. Y-directed displacement component, $\vec{U}_y$, could be derived from successive ultrasound frames in each plane at discrete locations and optionally interpolated to fill each image plane with displacement values. Note that the combination of the fast frame rate, relatively slow displacement compared to the frame rate, and the finite width of the "planes" in the elevation direction mean that the displacements are small between frames and that even when a point object in one frame is displaced in 3D, relative to that prior frame, in the next frame, the displacement may still be visible in the ultrasound "plane" image, allowing the in-plane component of the displacement to be determined even with a 3D movement between planes.

The assumption of radial displacement decay, away from the source can then be used to construct a 3D displacement field. For more complexly shaped probes, the contours will be more complexly shaped. Continuing with the hemispherical cap example, given the two planar measurements of $\vec{U}_y$ we can construct the 3D displacement field between two half planes, say the x-z plane in the +z direction and the x-y plane in the +x direction, by defining a polar coordinates system with origin at the Cartesian origin and with θ measured from the +z axis: the sagittal half plane being at θ=0 and the axial half plane being at θ=π/2. A linear radial interpolation can then be accomplished within the y=0 (x-z) plane, using the values of $\vec{U}_y$ measured within each plane, along each axis. One interpolator has the form;

$$\vec{U}_y(r,\theta)|_{y_i} = \vec{U}_{y_S}(r,0) + \text{Sgn}(\vec{U}_{y_S}(r,0) - \vec{U}_{y_A}(r,\tfrac{\pi}{2}))$$

-continued $$\tfrac{2\theta}{\pi}(\vec{U}_{y_A}(r,\tfrac{\pi}{2}) - \vec{U}_{y_S}(r,0))\text{Sgn}(\vec{U}_{y_A}(r,\tfrac{\pi}{2}) - \vec{U}_{y_S}(r,0))$$

Where: $\vec{U}_y(r,\theta)|_{y_i}$ is the y-directed component of displacement as a function of r and θ, where 0≤r≤Min(Max($z_S$), Max($x_A$)), and $$0 \le \theta \le \frac{\pi}{2}.$$

$\vec{U}_{y_S}(r,0)$ is the y-directed component of displacement in the sagittal plane (S-subscript). Similarly for $$\vec{U}_{y_A}(r,\tfrac{\pi}{2}).$$

Sgn is the Signum function:

$$\text{Sgn}(x) = \begin{array}{ll} 1 & x > 0 \\ 0 & x = 0 \\ -1 & x < 0 \end{array}$$

$y_i$ are the x-z planes for which y-directed displacement components have been obtained in the axial and sagittal planes: the equation for $\vec{U}_y(r,\theta)$ is evaluated at each of these planes to construct the 3D displacement field within the given quadrant.

The axially reflected quadrant can be obtained similarly. Moving along the axis of the probe, away from the hemispherical end cap, displacements measured towards the end of the sagittal plane may be fairly constant, may decay or increase, depending upon the locus of contact and the displacement applied. Decay measured within the axial plane can be used to extrapolate the decays measured within the rest of the sagittal plane, assuming a similar decay in the axial azimuths at each measurement location within the sagittal plane: the displacements within the sagittal plane modulate the extrapolated axial plane displacements. Other displacement components measured within the two planes could be similarly interpolated and extrapolated to obtain a 3D displacement field from all displacement components measured on the two planes. Of course, different assumptions and/or physical information could be used to derive different functional forms for the decay, and used to interpolate/extrapolate the 3D displacement field Even with only a single plane, for example the sagittal plane, it is possible to obtain a 3D displacement field, assuming that the rate of decay away from the probe displacement is equivalent in the other directions. Thus, we would obtain $$\frac{\partial \vec{U}_y}{\partial x_+} \text{ and } \frac{\partial \vec{U}_y}{\partial x_-},$$

in the axial plane, where:

$$\frac{\partial \vec{U}_y}{\partial z_+} = \frac{\partial \vec{U}_y}{\partial x_+} = \frac{\partial \vec{U}_y}{\partial x_-}$$

and similarly for all angles between the ±x and +z axes directions. Moving back along the probe, decay of the y-component of the displacement field would again be constructed by modulating the axial plane result with the measured displacement in the sagittal plane. The result of the two planes or the single plane is a 3D displacement field generated from measurements on two planes.

Figure 9:
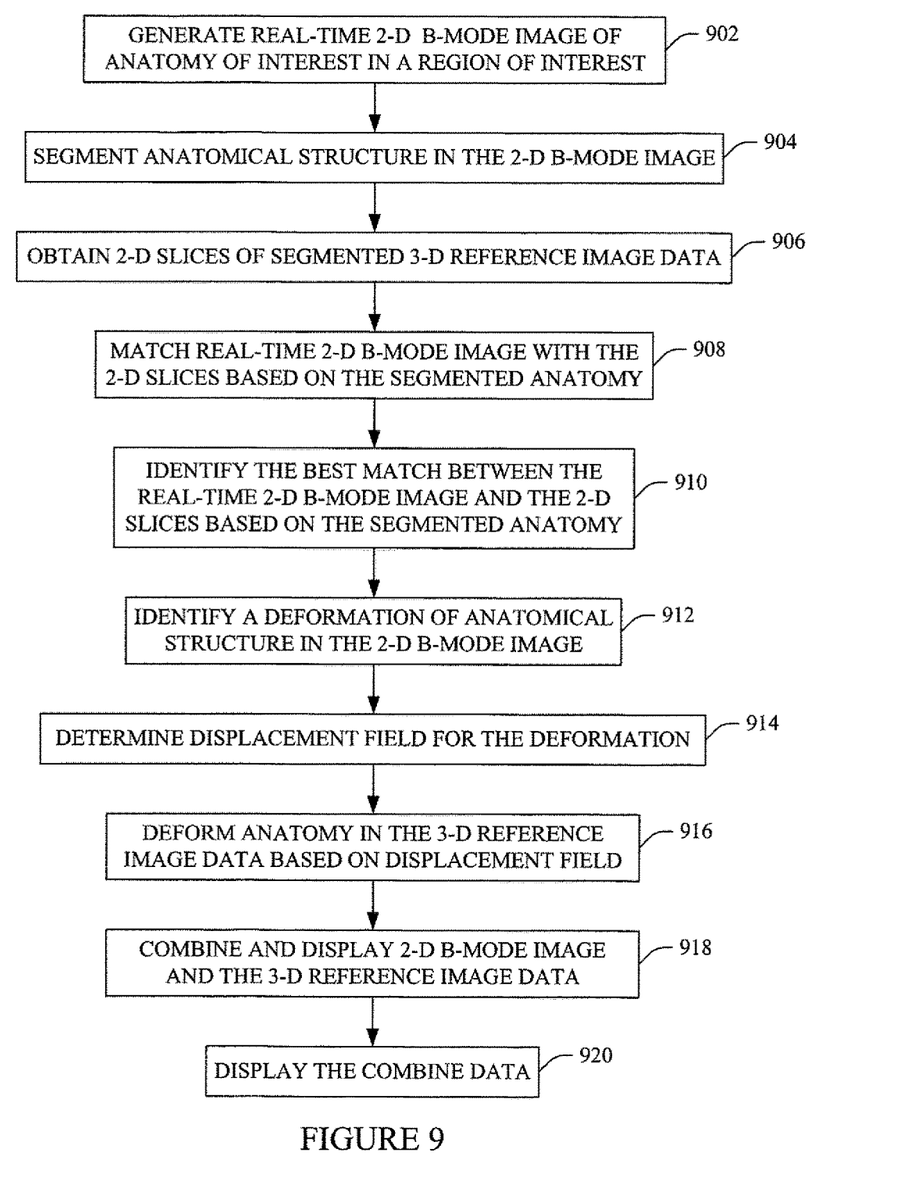
FIG. 9 illustrates an example method in accordance with an embodiment herein.

FIG. 9 illustrates an example method in accordance with an embodiment herein.

It is to be appreciated that the ordering of the above acts is not limiting. As such, other orderings are contemplated herein. In addition, one or more acts may be omitted and/or one or more additional acts may be included.

At 902, a real-time 2-D B-mode image of anatomy of interest in a region of interest is generated by the imaging system 100 with echoes received by the transducer elements 106 of the imaging system 100.

At 904, one or more anatomical features are segmented from the real-time 2-D B-mode image, as described herein and/or otherwise.

At 906, one or more 2-D slices from anatomically segmented 3-D reference image data for the region of interest are obtained.

At 908, the real-time 2-D B-mode image is matched to the 2-D slices of the anatomically segmented 3-D reference image data, as described herein and/or otherwise.

Acts 906 and 908 can occur simultaneously if a 2D slice is extracted and matched against in an iterative fashion. Having at least some starting slices would facilitate narrowing down the location(s) for further match tries.

At 910, the 2-D slice of the anatomically segmented 3-D reference image data that best matches the real-time 2-D B-mode image is identified, as described herein and/or otherwise.

At 912, a deformation of anatomical structure in the 2-D B-mode image is identified, as described herein and/or otherwise.

At 914, a displacement field is determined for the deformed anatomical structure between the 2-D B-mode image and the 3-D reference image data, as described herein and/or otherwise.

At 916, at least a sub-portion of the anatomy in the 3-D reference image data is deformed to correspond to a location of the same anatomy in the 2-D B-mode image using the displacement field, as described herein and/or otherwise.

At 918, the 2-D B-mode image is combined with the deformed anatomically segmented 3-D reference image data at the location of the matched planar slice.

At 920, the combined image is displayed.

At least a portion of the methods discussed herein may be implemented by way of computer readable instructions, encoded or embedded on computer readable storage medium (which excludes transitory medium), which, when executed by a computer processor(s), causes the processor(s) to carry out the described acts. Additionally or alternatively, at least one of the computer readable instructions is carried by a signal, carrier wave or other transitory medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method, comprising:
    generating a real-time ultrasound image of an anatomy of interest of a subject being scanned, wherein the real-time ultrasound image is currently generated from ultrasound echoes currently acquired during the scan, and at least a sub-portion of the anatomy of interest is deformed from an initial location to a different location by pressure applied by an external force;
    obtaining, during the scan, a 2-D slice, which corresponds to a same plane as the real-time ultrasound image, from previously acquired 3-D reference image data, wherein a corresponding sub-portion is at the initial location;
    determining, during the scan, displacement fields for the sub-portion from the different location of the sub-portion, the initial location of the corresponding sub-portion, a location of other anatomy in the real-time ultrasound image, and a location of the other anatomy the 3-D reference image data, wherein the location of other anatomy in the real-time ultrasound image and the location of the other anatomy the 3-D reference image data have overlapping image coordinates, the other anatomy is not-deformed in the real-time ultrasound image by the pressure applied by the external force, and the other anatomy is not-deformed in the 3-D reference image data by the pressure applied by the external force,
    wherein the real-time ultrasound image and the 3-D reference image data include common segmented structures, and further comprising:
        determining a displacement of the sub-portion from the contours of the sub-portion, the corresponding sub-portion and the other anatomy not deformed in the real-time ultrasound image and the 2-D slice;
        measuring a first distance between a contour of the sub-portion and a contour of the other anatomy in the real-time ultrasound image;
        measuring a second distance between a corresponding contour of the corresponding sub-portion and a corresponding contour of the other anatomy in the 2-D slice; and
    determining a differential displacement of the sub-portion from the first and second distance; and
    deforming, during the scan, the 3-D reference image data using the displacement fields, which creates deformed 3-D reference image data based on the different location, wherein the displacement field is determined with the differential displacement.

2. The method of claim 1, wherein deforming the 3-D reference image data includes re-positioning the sub-portion in the 3-D reference image data at a location in the 3-D reference image data that corresponds to a corresponding location of the sub-portion in the real-time ultrasound image.

3. The method of claim 1, further comprising:
    combining the real-time ultrasound image with the deformed 3-D reference image data at a corresponding plane in the 3-D reference image data; and
    displaying the combined data.

4. The method of claim 1, further comprising: identifying the sub-portion from contours of the common segmented structures in both the real-time ultrasound image and the 2-D slice.

5. The method of claim 1, wherein the displacement represents an indentation along, at least, a finite length of an image plane.

6. The method of claim 1, wherein the deforming of the 3-D reference image data includes mapping anatomical structures within the 3-D reference image data to deformed locations based on a deformation of the sub-portion.

7. The method of claim 6, wherein the mapping applies directional derivatives of the displacement fields, including a left direction and a right direction, relative to a maximum displacement vector in a probe plane, to map the anatomical structures within the 3-D reference image data to the deformed locations based on the deformation of the sub-portion.

8. The method of claim 7, wherein the mapping further uses cylindrical symmetry of the directional derivatives.

9. The method of claim 7, wherein the mapping further uses a transition between two differing derivatives orthogonal to a single plane.

* * * * *

UNITED STATES PATENT AND TRADEMARK OFFICE
CERTIFICATE OF CORRECTION

PATENT NO. : 11,064,979 B2  
APPLICATION NO. : 15/155397  
DATED : July 20, 2021  
INVENTOR(S) : Lieblich et al.

Page 1 of 1

It is certified that error appears in the above-identified patent and that said Letters Patent is hereby corrected as shown below:

On the Title Page

Column 1, in item (73) Assignee delete:
"Analogic Corporation"
And insert:
--BK Medical Holding Company, Inc. Peabody, MA (US)--

Signed and Sealed this
Sixteenth Day of August, 2022

Katherine Kelly Vidal
*Director of the United States Patent and Trademark Office*